United States Patent
Kawahara et al.

(10) Patent No.: US 6,844,465 B2
(45) Date of Patent: Jan. 18, 2005

(54) METHOD FOR PREPARING HIGHLY STABLE CRYSTALS OF ASPARTAME DERIVATIVE

(75) Inventors: Shigeru Kawahara, Kawasaki (JP); Akihiro Kishishita, Kawasaki (JP); Kazutaka Nagashima, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/160,000

(22) Filed: Jun. 4, 2002

(65) Prior Publication Data

US 2002/0193621 A1 Dec. 19, 2002

Related U.S. Application Data

(63) Continuation of application No. 09/830,158, filed as application No. PCT/JP99/06083 on Nov. 1, 1999, now abandoned.

(30) Foreign Application Priority Data

Oct. 30, 1998 (JP) ............................................ 10-310227
Oct. 30, 1998 (JP) ............................................ 10-310228

(51) Int. Cl.[7] .......................................... C07C 229/00
(52) U.S. Cl. ...................................................... 560/40
(58) Field of Search ........................................... 560/40

(56) References Cited

U.S. PATENT DOCUMENTS 4,579,747 A * 4/1986 Sugiyama et al.
4,835,303 A * 5/1989 Wakamatsu et al.
5,480,668 A * 1/1996 Nofre et al.
5,510,508 A    4/1996 Claude et al.
5,543,554 A    8/1996 Ohura et al.
5,728,862 A    3/1998 Prakash
5,773,640 A    6/1998 Nofre et al.

FOREIGN PATENT DOCUMENTS

| EP | 0 362 706 | 4/1990 |
|---|---|---|
| WO | WO 95/30688 | 11/1995 |
| WO | WO 95/30689 | 11/1995 |

OTHER PUBLICATIONS

M. Hatada, et al., *J. Am. Chem. Soc.*, vol. 107, pp. 4279–4282 (1985).

* cited by examiner

*Primary Examiner*—Paul A. Zucker
(74) *Attorney, Agent, or Firm*—Oblon, Spivak, McClelland, Maier & Neustadt, P.C.

(57) ABSTRACT

Disclosed in the present application are a method for preparing highly-stable A-type crystals by controlling and maintaining the product temperature of B-type N-(3,3-dimethylbutyl)-APM crystals at 25 to 80° C. under an absolute humidity of 0.203 kg/kg or less environment, thereby effecting crystal transition; and a method for preparing A-type crystals by controlling and maintaining the product temperature of D-type crystals of N-(3,3-dimethylbutyl)-APM at 25 to 80° C. under an absolute humidity of 0.0550 kg/kg or less environment, thereby effecting crystal transition. According to these crystal transition methods, highly stable crystals can be prepared stably and at a low cost.

16 Claims, 4 Drawing Sheets

METHOD FOR PREPARING HIGHLY STABLE CRYSTALS OF ASPARTAME DERIVATIVE

This application is a continuation of U.S. patent application Ser. No. 09/830,158 filed Jun. 27, 2001, now abandoned, which is a 371 of PCT/JP99/06083 filed Nov. 1, 1999.

TECHNICAL FIELD

The present invention relates to a process for preparing the highly stable crystals of N-[N-(3,3-dimethylbutyl)-L-α-aspartyl]-L-phenylalanine methyl ester, which is a high intensity sweetener. L-α-aspartyl-L-phenylalanine methyl ester is, as is well known, one of amino acid type high intensity sweeteners which has already been commercialized, and it is abbreviated as APM or aspartame. The sweetening substance relating to the present invention is therefore considered as an APM or aspartame derivative, and will hereinafter be abbreviated as N-(3,3-dimethylbutyl)-APM. Additionally, this sweetening substance is abbreviated as Neotame in some publications.

BACKGROUND ART

N-(3,3-dimethylbutyl)-ATM has a sweetening potency, on the weight basis, of at least 50 times that of aspartame and about 10,000 times that of sucrose (table sugar) so that it can constitute a high intensity sweetener.

Since sweetening agents are mainly employed in foods for human consumption, they must be prepared using a method which can provide a highly purified product substantially free from impurities or decomposition products. Furthermore, in the case of a sweetener which tends to be decomposed relatively easily, like N-(3,3-dimethylbutyl)-APM, some countermeasures are required against the decomposition thereof after forwarded as a product.

The already known crystals of N-(3,3-dimethylbutyl)-APM are described in WO95/30689 with reference to the IR spectrum data. The present inventors have confirmed that these crystals are monohydrate crystals as a result of X-ray-crystal structure analysis, and that they show the specific peaks of diffracted X-rays at angles of diffraction of at least 6.0°, 24.8°, 8.2° and 16.5° when measured by a powder X-ray diffractometer using CuKα radiation. The present inventors have decided to call these crystals "A-type crystal" for convenience' sake.

Meanwhile, a preparation process of N-(3,3-dimethylbutyl)-APM is also described in U.S. Pat. No. 5,278,862, wherein high purity (97% by HPLC) N-(3,3-dimethylbutyl)-APM is obtained by spontaneous crystallization using methanol and water as the crystallization solvent.

And, the present inventors have followed Example 1 of the said U.S. Pat. No. 5,278,862. As the results, although they have confirmed the reproducibility of the data on purity (98% by HPLC), they could not confirm the formation of A-type crystals. In greater detail, the N-(3,3-dimethylbutyl)-APM obtained by following the said Example 1, showed, as wet crystals, the specific peaks of diffracted X-rays at angles (2θ, CuKα rays) of diffraction of at least 5.1°, 21.1°, 21.3° and 8.3°. The powder X-ray diffraction pattern at this time will be given in FIG. 1. These crystals will hereinafter be called "B-type crystal".

Furthermore, the B-type crystals obtained by following Example 1 of the said U.S. Pat. No. 5,728,862, when dried, gave crystals exhibiting the specific peaks of diffracted X-rays at angles (2θ, CuKα rays) of diffraction of at least 5.6°, 8.4°, 17.1° and 18.8°. The powder X-ray diffraction pattern at this time will be given in FIG. 2. As a result of measurement by the Karl Fisher's method, the water content of these crystals were found to be 0.6 wt. %. These crystals will hereinafter be called "G-type crystal".

On the other hand, the present inventors have found that novel crystals of N-(3,3-dimethylbutyl)-APM exhibiting the specific peaks of diffracted X-rays at angles (2θ, CuKα rays) of diffraction of at least 5.4°, 8.4°, 18.8° and 17.6°, can be obtained by drying B-type crystals until their water content comes to 3 to 6 wt. %. These novel crystals will hereinafter be called "D-type crystal" for convenience' sake. The powder X-ray diffraction pattern at this time will be shown in FIG. 3.

Then, the obtained G-type crystals, D-type crystals and A-type crystals of N-(3,3-dimethylbutyl)-APM were tested at 70° C., concerning their stability. As a result, after the lapse of 271 hours, the remaining ratio of the N-(3,3-dimethylbutyl)-APM in the form of the G-type crystals and that in the form of the D-type crystals were 18 wt. % and 77 wt. %, respectively, while that in the form of the A-type crystals was 96 wt. %, suggesting that N-(3,3-dimethylbutyl)-APM is most stable in the form of A-type crystals. The relationship between the storage time and the remaining ratio of N-(3,3-dimethylbutyl)-APM in this test will be shown below in Table 1.

TABLE 1

Stability test at 70° C.

| Crystal type | Time elapsed (hrs) | | |
|---|---|---|---|
| | 0 Remaining Ratio (wt. %) | 100 Remaining ratio (wt. %) | 271 Remaining Ratio (wt. %) |
| A | 95 | 94 | 96 |
| D | 95 | 96 | 77 |
| G | 96 | 48 | 18 |

As described above, it has been found that according to Example 1 of U.S. Pat. No. 5,728,862, G-type crystals of N-(3,3-dimethylbutyl)-APM which are inferior to A-type crystals in stability, are obtained.

DISCLOSURE OF THE INVENTION

As has been described above, a process for stably preparing A-type crystals excellent in stability, of N-(3,3-dimethylbutyl)-APM at a low cost, has not yet been established in the existing state of art.

Therefore, it is an object of the present invention to provide a process for stably and conveniently preparing highly stable A-type crystals of N-(3,3-dimethylbutyl)-APM, which is a high intensity sweetener, from B-type crystals of N-(3,3-dimethylbutyl)-APM exhibiting the specific peaks of diffracted X-rays at angles of diffraction (2θ, CuKα rays) of at least 5.1°, 21.1°, 21.3° and 8.3°. It is another object of the present invention to provide a process for stably and conveniently preparing highly stable A-type crystals of N-(3,3-dimethylbutyl)-APM, which is a high intensity sweetener, from D-type crystals of N-(3,3-dimethylbutyl)-APM exhibiting the specific peaks of diffracted X-rays at angles of diffraction (2θ, CuKα rays) of at least 5.4°, 8.4°, 18.8° and 17.6° in the diffracted X-rays.

With a view to attaining the above-described objects, the present inventors have carried out an extensive and intensive investigation. As a result, it has been found that when B-type crystals of N-(3,3-dimethylbutyl)-APM are maintained in their temperature under a certain absolute humidity atmosphere, the crystal transition from the B-type crystals to A type crystals proceeds; and that by keeping the temperature of D-type crystals of N-(3,3-dimethylbutyl)-APM under an appropriate absolute humidity atmosphere, the crystal transition from the D-type crystals to A type crystals also proceeds. Based on such findings, the present invention has been completed.

Accordingly, the present invention relates, in a first aspect, to a method for preparing highly stable crystals (A-type crystals) of N-[N-(3,3-dimethylbutyl)-L-α-aspartyl]-L-phenylalanine methyl ester characterized by the peaks at at least 6.0°, 24.8°, 8.2° and 16.5°, which comprises controlling and maintaining, under an absolute humidity of 0.203 kg/kg or less environment or atmosphere, the temperature of wet crystals (B-type crystals) of N-[N-(3,3-dimethylbutyl)-L-α-aspartyl]-L-phenylalanine methyl ester exhibiting the specific peaks of diffracted X-rays at angles of diffraction (2θ, CuKα rays) of at least 5.1°, 21.1°, 21.3° and 8.3°, at 25 to 80° C., whereby the crystal transition from the B-type crystals to A-type crystals is allowed to be effected, and in a second aspect, to a method for preparing highly stable crystals (A-type crystals) of N-[N-(3,3-dimethylbutyl)-L-α-aspartyl]-L-phenylalanine methyl ester characterized by the peaks at at least 6.0°, 24.8°, 8.2° and 16.5°, which comprises controlling and maintaining, under an absolute humidity of 0.0550 kg/kg or less atmosphere, the temperature of crystals (D-type crystals) of N-[N-(3,3-dimethylbutyl)-L-α-aspartyl]-L-phenylalanine methyl ester exhibiting the specific peaks of diffracted X-rays at angles (2θ, CuKα rays) of diffraction of at least 5.4°, 8.4°, 18.8° and 17.6°, at 25 to 80° C., whereby the crystal transition from the D-type crystals to A-type crystals is allowed to be effected.

In the first place, the first-mentioned crystal preparation method (crystal transition method) will hereinafter be described.

According to the present crystal transition method, temperatures at which wet B-type crystals of N-(3,3-dimethylbutyl)-APM should be maintained, are preferably 25 to 80° C. At lower temperatures, crystal transition to A-type crystals does not proceed or even if it proceeds, the transition speed is slow. At too high temperatures, on the other hand, decomposition of crystals inevitably occurs. According to the present crystal transition method, the absolute humidity under which the wet B-type crystals should be maintained, is preferably 0.203 kg/kg or less, because it takes longer time for the crystal transition under too high a humidity.

It is needless to say that the crystal transition according to the present invention is not influenced by the preparation method of N-(3,3-dimethylbutyl)-APM or that of B-type crystals thereof.

The present crystal transition method is characterized in that A-type crystals of N-(3,3-dimethylbutyl)-APM can be obtained from B-type crystals thereof. Such crystal transition method can be effected by realizing the crystal transition conditions of the present invention in a dryer and drying the resulting A type crystals until their water content gets to 3 to 6 wt. %. Such a mode is preferred.

In the next place, description will be made of the second-mentioned crystal transition method according to the present invention.

According to the present crystal transition method, temperatures at which D-type crystals of N-(3,3-dimethylbutyl)-APM should be maintained, are preferably 25 to 80° C. At lower temperatures, crystal transition to A-type crystals does not proceed or even if it proceeds, the transition speed is slow, and at too high temperatures, on the other hand, decomposition of crystals inevitably occurs. This is the same as has been described in connection with the first-mentioned crystal transition method. According to the present crystal transition method, the absolute humidity under which the D-type crystals should be maintained, is preferably 0.0550 kg/kg or less, because it takes longer time for the crystal transition under too high a humidity. This is also the same as has been described in connection with the first-mentioned crystal transition method.

It is needless to say that the crystal transition according to the present invention is not influenced by the preparation method of N-(3,3-dimethylbutyl)-APM or that of D-type crystals thereof.

The present crystal transition method is characterized in that A-type crystals of N-(3,3-dimethylbutyl)-APM can be obtained from D-type crystals thereof. Such crystal transition method can also be effected by realizing the crystal transition conditions of the present invention in a dryer and drying the resulting A-type crystals until their water content gets to 3 to 6 wt. %. Such a mode is preferred.

BEST MODE FOR CARRYING OUT THE INVENTION

Figure 1:
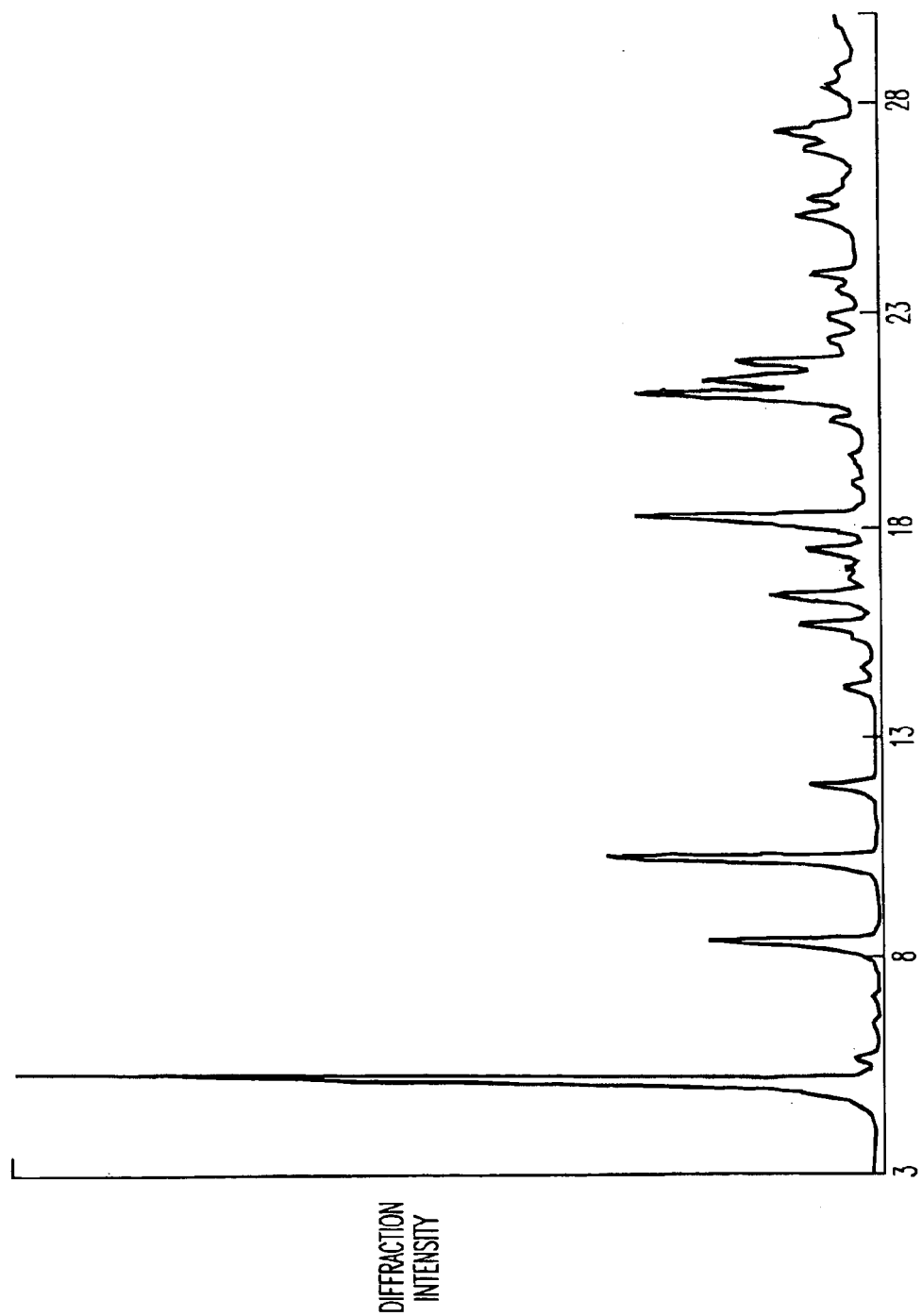
FIG. 1 shows a powder X-ray diffraction pattern of the B-type crystals.
Figure 2:
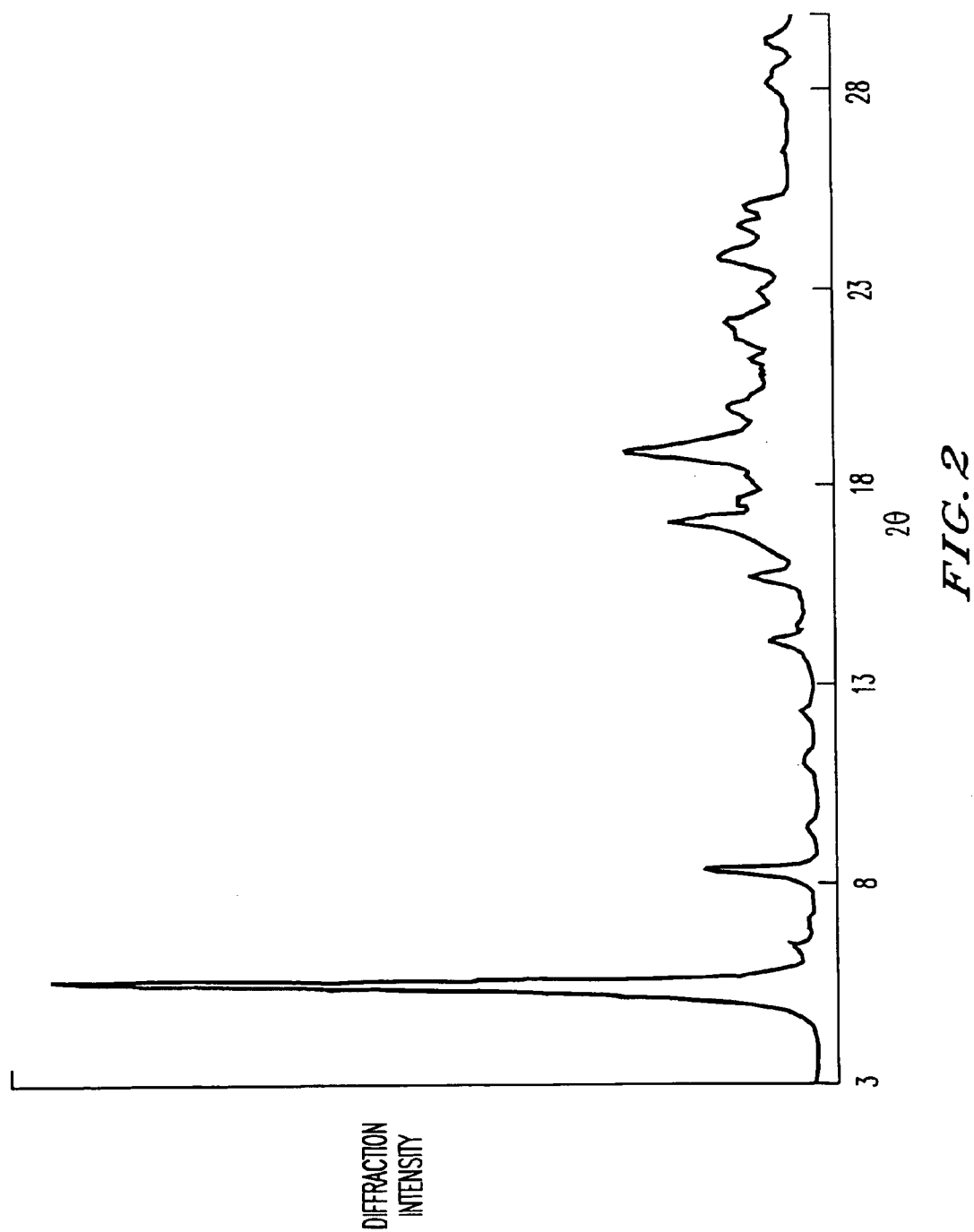
FIG. 2 shows a powder X-ray diffraction pattern of the G-type crystals.

The present invention will hereinafter be described more specifically with reference to Examples.

In the first place, Examples of the first-mentioned crystal transition method will be described.

Referencial Example 1

Preparation of A-type Crystals of N-(3,3-dimethylbutyl)-APM

In a reactor being equipped with an agitating blade and permitting markedly smooth transfer of gaseous hydrogen into the liquid layer, the following substances were charged with stirring: 550 mL of ion-exchanged water, 1,100 mL of methanol, 61 g of aspartame, 20 g of 10% palladium-carbon (having a water content of 50 wt. %) and 19 g of 3,3-dimethylbutyl aldehyde.

After the completion of charging, hydrogen gas was introduced at a flow rate of 200 mL/min while the mixture was continued to be stirred at room temperature. The progress of the reaction was monitored by sampling the reaction mixture and analyzing the resulting products in the samples by high-performance liquid chromatography (HPLC). After six hours' reaction, the reactor was filled with a nitrogen gas stream, followed by filtration through a microporous filter (0.50 μm) to remove the catalyst. The filtrate (1,460 g), when analyzed, revealed that the N-(3,3-dimethylbutyl)-APM had been produced in an amount of 64 g (yield: 85%).

The filtrate was then concentrated to 497 g, whereby crystals were precipitated. The resulting slurry was heated at 70° C. to dissolve the crystals. Then, the resulting solution was analyzed by gas chromatography, and revealed that the methanol content in the solution was 8.15 wt. %.

Subsequently, this homogeneous solution of N-(3,3-dimethylbutyl)-APM was gradually cooled from 70° C. to 40° C. and maintained at 40° C. for 1 hour, whereby nucleation was allowed to occur spontaneously.

Next, the resulting slurry was then cooled to 5° C. at a cooling rate of 5° C./hour, and aged overnight at this temperature, followed by separating the crystals by filtration. The wet crystals were then dried at 50° C. under reduced pressure until the water content became 5.8 wt. %, whereby 58 g of N-(3,3-dimethylbutyl)-APM was obtained (yield: 72%, and a purity of 97% by HPLC).

Referential Example 2

Into a three-necked flask, 22 g of N-(3,3-dimethylbutyl)-APM obtained in Referential Example 1 was charged, followed by the addition of 22 g of methanol and 104 g of water. The resulting mixture was heated to 70° C. to completely dissolve the crystals in the solvent, whereby a solution having a methanol content of 15 wt. % in terms of the concentration in the whole solution was prepared. This container having the solution therein was equipped with an agitating blade, thermometer and the like, and then dipped in a water bath of 25° C. to cool the solution. When the temperature of the solution became 25° C., spontaneous nucleation occurred. After the crystals were aged for 2 hours in the water bath of 25° C., the resulting crystals were collected by filtration.

As a result of measuring the diffracted X-rays of the wet crystals thus collected, by using CuKα rays in accordance with the powder X-ray diffraction method, they showed the specific peaks of diffracted X-rays at angles (2θ, CuKα rays) of diffraction of at least 5.1°, 21.1°, 21.3° and 8.3°, indicating that the resulting crystals were B-type crystals.

EXAMPLE 1

The B-type crystals obtained in Referential Example 2 were allowed to stand, for one hour, in a thermostat in which the absolute humidity and the product temperature were adjusted as shown below in Table 2. The crystal type of the resulting crystals of N-(3,3-dimethylbutyl)-APM was studied by the powder X-ray diffraction method. The results as shown in Table 2 were obtained.

TABLE 2

| Crystal transition conditions | Absolute humidity (kg/kg) | Product temperature (° C.) | Crystal type |
|---|---|---|---|
| (1) | 0.00726 | 20 | B |
| (2) | 0.0250 | 40 | A |

EXAMPLE 2

The B-type crystals obtained in Referential Example 2 were allowed to stand for 20 minutes in a hot air flow dryer (the flow rate of hot air: 1 m³/sec). The crystal type of the resulting N-(3,3-dimethylbutyl)-APM crystals was studied by the powder X-ray diffraction method. The results as shown below in Table 3 were obtained. In greater detail, crystals showing the specific peaks of diffracted X-rays at angles (2θ, CuKα rays) of diffraction of at least 6.0°, 24.8°, 8.2° and 16.5°, were obtained under the condition of the product temperature of 35 to 60° C. and absolute humidity of 0.00417 to 0.08320 kg/kg. Based on these results, the crystals were identified as A-type crystals.

TABLE 3

| Crystal transition conditions | Absolute humidity (kg/kg) | Product temperature (° C.) | Crystal type |
|---|---|---|---|
| (3) | 0.00579 | 20 | B |
| (4) | 0.00417 | 35 | A |
| (5) | 0.02890 | 35 | A |
| (6) | 0.08320 | 60 | A |

In the next place, description will be made of the examples of the second-mentioned crystal transition method.

Referential Example 3

Figure 3:
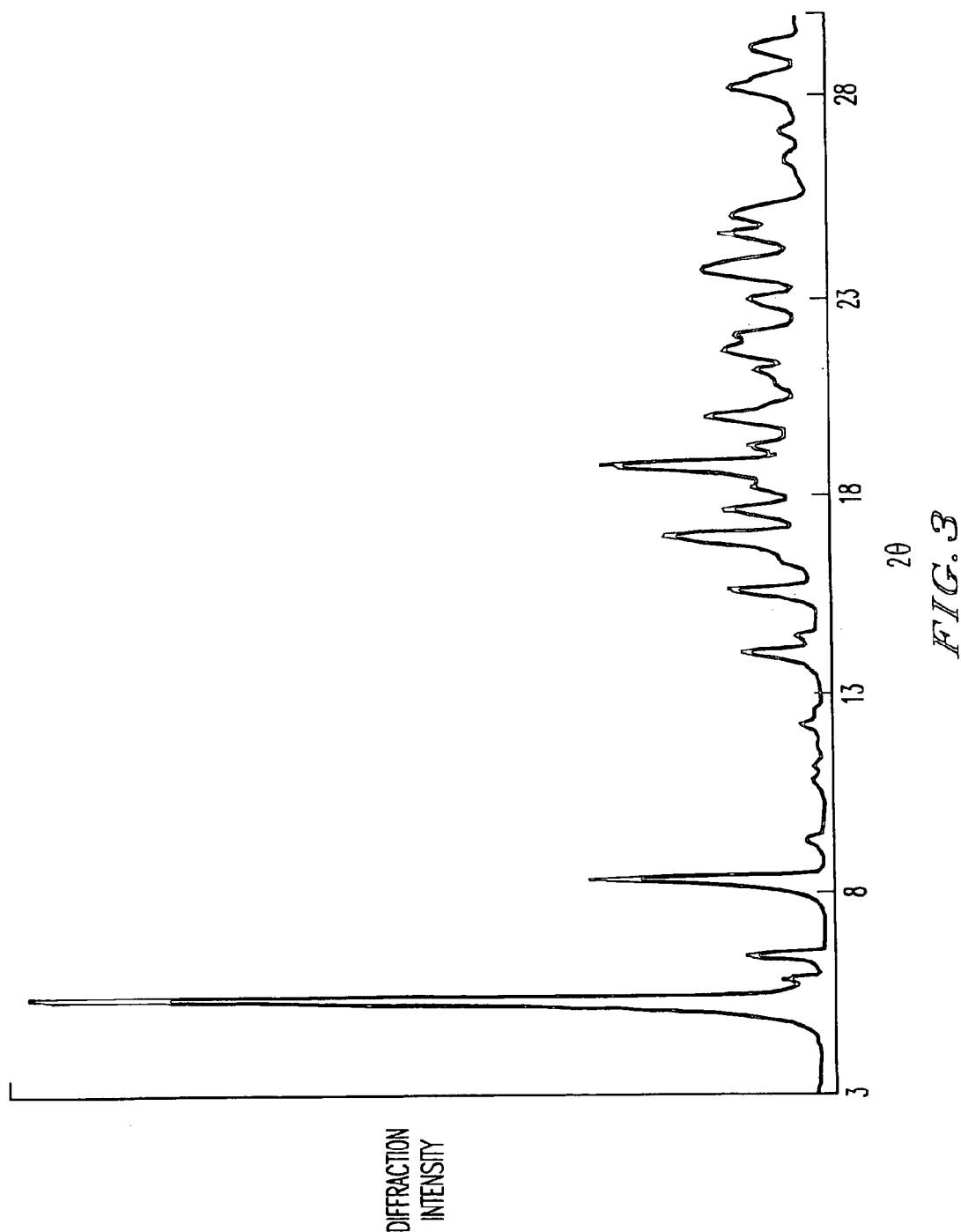
FIG. 3 shows a powder X-ray diffraction pattern of the D-type crystals.
Figure 4:
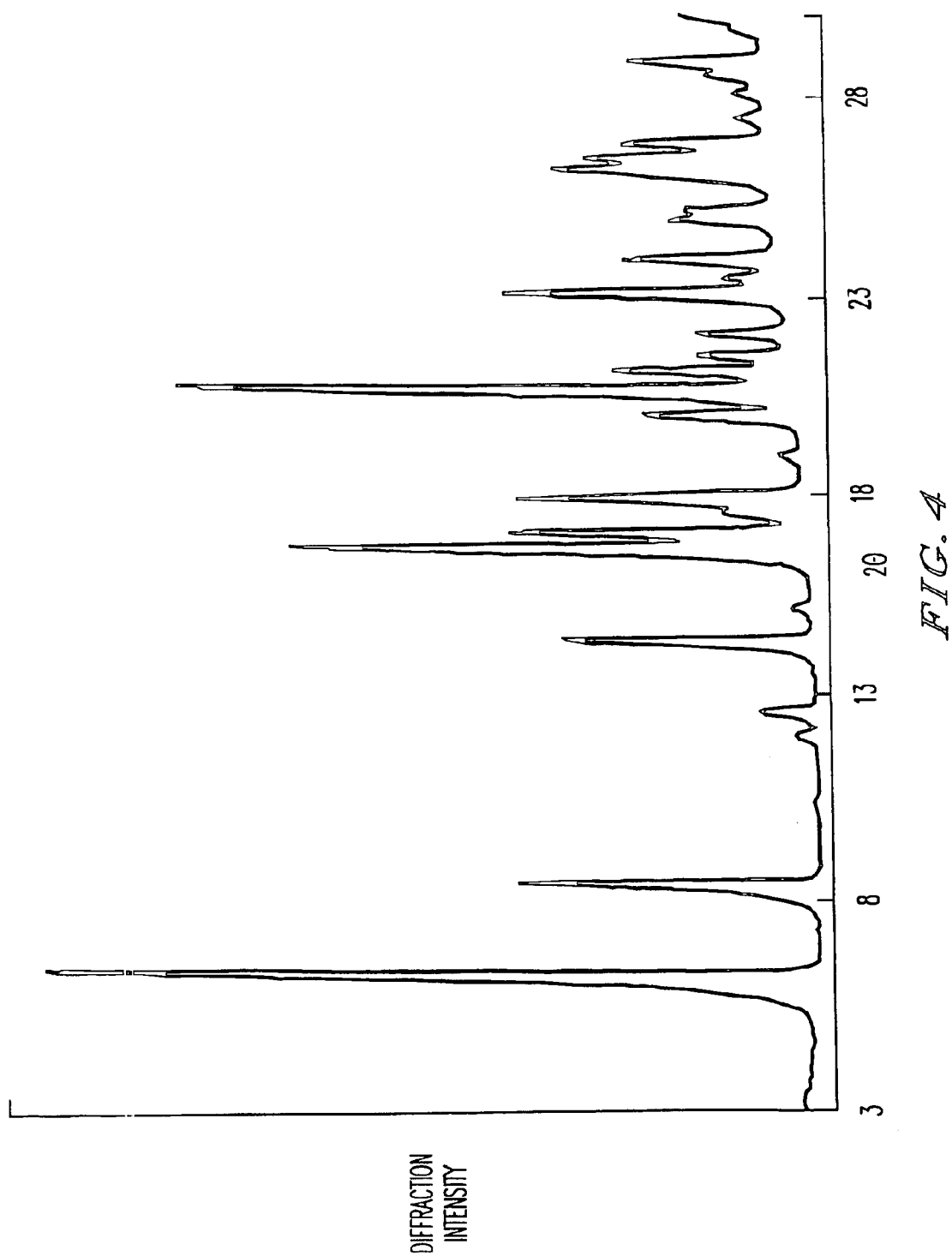
FIG. 4 shows a powder X-ray diffraction patter of the A-type crystals.

The B-type crystals obtained above in Referential Example 2 were dried at 25° C. or less under reduced pressure in a vacuum dryer until their water content reached 4.6 wt. %. As a result of measuring the diffracted X-rays by using CuKα rays in accordance with the powder X-ray diffraction method, the wet crystals thus obtained showed the specific peaks of diffracted X-rays at angles (2θ, CuKα rays) of diffraction of at least 5.4°, 8.4°, 18.8° and 17.6°, indicating that the resulting crystals were D-type crystals (refer to FIG. 3).

Example 3

The D-type crystals obtained in Referential Example 3 above were allowed to stand, for 2 hours, in a thermostat in which the absolute humidity and the product temperature were adjusted as shown below in Table 4. The crystal type of the resulting crystals of N-(3,3-dimethylbutyl)-APM was studied by the powder X-ray diffraction method. The results as shown in Table 4 were obtained. In greater detail, crystals showing the specific peaks of diffracted X-rays at angles (2θ, CuKα rays) of diffraction of at least 6.0°, 24.8°, 8.2° and 16.5°, were obtained under the condition of the product temperature of 30 to 50° C. and absolute humidity of 0.0133 to 0.0403 kg/kg. Based on these results, the crystals were identified as A-type crystals.

TABLE 4

| Crystal transition conditions | Absolute humidity (kg/kg) | Product temperature (° C.) | Crystal type |
|---|---|---|---|
| (7) | 0.0043 | 20 | D |
| (8) | 0.0133 | 30 | A |
| (9) | 0.0220 | 40 | A |
| (10) | 0.0403 | 50 | A |

Industrial Applicability

A-type crystals excellent in stability, of N-(3,3-dimethylbutyl)-APM, which is a high intensity sweetener, can be obtained conveniently and at a low cost by the crystal transition of B-type or D-type crystals of N-(3,3-dimethylbutyl)-APM.

What is claimed is:

1. A method for preparing A-type crystals of N-[N-(3,3-dimethylbutyl)-L-α-aspartyl]-L-phenylalanine methyl ester, said method comprising:

(a) maintaining B-type crystals of N-[N-(3,3-dimethylbutyl)-L-α-aspartyl]-L-phenylalanine methyl ester in an environment having an absolute humidity of 0.203 kg/kg or less and a temperature of 25 to 80° C., to convert said B-type crystals to said A-type crystals.

2. The method of claim 1, wherein said A-type crystals of N-[N-(3,3-dimethylbutyl)-L-α-aspartyl]-L-phenylalanine methyl ester exhibit a CuKα x-ray powder diffraction pattern having characteristic peaks at 2θ angles of 6.0°, 24.8°, 8.2°, and 16.5°.

3. The method of claim 1, wherein said B-type crystals of N-[N-(3,3-dimethylbutyl)-L-α-aspartyl]-L-phenylalanine methyl ester exhibit a CuKα x-ray powder diffraction pattern having characteristic peaks at 2θ angles of 5.1°, 21.1°, 21.3°, and 8.3°.

4. The method of claim 1, wherein said A-type crystals of N-[N-(3,3-dimethylbutyl)-L-α-aspartyl]-L-phenylalanine methyl ester exhibit a CuKα x-ray powder diffraction pattern having characteristic peaks at 2θ angles of 6.0°, 24.8°, 8.2°, and 16.5° and said B-type crystals N-[N-(3,3-dimethylbutyl)-L-α-aspartyl]-L-phenylalanine methyl ester exhibit a CuKα x-ray powder diffraction pattern having characteristic peaks at 2θ angles of 5.1°, 21.1°, 21.3°, and 8.3°.

5. The method of claim 4, wherein said A-type crystals of N-[N-(3,3-dimethylbutyl)-L-α-aspartyl]-L-phenylalanine methyl ester have a water content of 3 to 6 wt. %.

6. The method of claim 1, wherein said B-type crystals of N-[N-(3,3-dimethylbutyl)-L-α-aspartyl]-L-phenylalanine methyl ester are maintained in an environment having an absolute humidity of 0.00417 to 0.08320 kg/kg.

7. The method of claim 1, wherein said B-type crystals of N-[N-(3,3-dimethylbutyl)-L-α-aspartyl]-L-phenylalanine methyl ester are maintained in an environment having a temperature of 35 to 60° C.

8. The method of claim 1, wherein said B-type crystals of N-[N-(3,3-dimethylbutyl)-L-α-aspartyl]-L-phenylalanine methyl ester are maintained in an environment having an absolute humidity of 0.00417 to 0.08320 kg/kg and a temperature of 35 to 60° C.

9. A method for preparing A-type crystals of N-[N-(3,3-dimethylbutyl)-L-α-aspartyl]-L-phenylalanine methyl ester, said method comprising:

(a) maintaining D-type crystals N-[N-(3,3-dimethylbutyl)-L-α-aspartyl]-L-phenylalanine methyl ester in an environment having an absolute humidity of 0.0550 kg/kg or less and a temperature of 25 to 80° C., to convert said D-type crystals to said A-type crystals.

10. The method of claim 9, wherein said A-type crystals of N-[N-(3,3-dimethylbutyl)-L-α-aspartyl]-L-phenylalanine methyl ester exhibit a CuKα x-ray powder diffraction pattern having characteristic peaks at 2θ angles of 6.0°, 24.8°, 8.2°, and 16.5°.

11. The method of claim 9, wherein said D-type crystals of N-[N-(3,3-dimethylbutyl)-L-α-aspartyl]-L-phenylalanine methyl ester exhibit a CuKα x-ray powder diffraction pattern having characteristic peaks at 2θ angles of 5.4°, 8.4°, 18.8°, and 17.6°.

12. The method of claim 9, wherein said A-type crystals of N-[N-(3,3-dimethylbutyl)-L-α-aspartyl]-L-phenylalanine methyl ester exhibit a CuKα x-ray powder diffraction pattern having characteristic peaks at 2θ angles of 6.0°, 24.8°, 8.2°, and 16.5° and said D-type crystals N-[N-(3,3-dimethylbutyl)-L-α-aspartyl]-L-phenylalanine methyl ester exhibit a CuKα x-ray powder diffraction pattern having characteristic peaks at 2θ angles of 5.4°, 8.4°, 18.8°, and 17.6°.

13. The method of claim 9, wherein said A-type crystals of N-[N-(3,3-dimethylbutyl)-L-α-aspartyl]-L-phenylalanine methyl ester have a water content of 3 to 6 wt. %.

14. The method of claim 9, wherein said D-type crystals of N-[N-(3,3-dimethylbutyl)-L-α-aspartyl]-L-phenylalanine methyl ester are maintained in an environment having an absolute humidity of 0.0133 to 0.0403 kg/kg.

15. The method of claim 9, wherein said D-type crystals of N-[N-(3,3-dimethylbutyl)-L-α-aspartyl]-L-phenylalanine methyl ester are maintained in an environment having a temperature of 30 to 50° C.

16. The method of claim 9, wherein said D-type crystals of N-[N-(3,3-dimethylbutyl)-L-α-aspartyl]-L-phenylalanine methyl ester are maintained in an environment having an absolute humidity of 0.0133 to 0.0403 kg/kg and a temperature of 30 to 50° C.

* * * * *